United States Patent

Yamamoto et al.

[11] Patent Number: 5,419,916
[45] Date of Patent: May 30, 1995

[54] GELATIN COATING COMPOSITION AND HARD GELATIN CAPSULE

[75] Inventors: Taizo Yamamoto, Osaka; Masato Kobayashi, Yamatokoriyama; Seinosuke Matsuura, Kyoto, all of Japan

[73] Assignee: Japan Elanco Company, Limited, Osaka, Japan

[21] Appl. No.: 95,417

[22] Filed: Jul. 22, 1993

[30] Foreign Application Priority Data

Aug. 27, 1992 [JP] Japan ................................ 4-252074

[51] Int. Cl.$^6$ .......................... A61K 9/40; A61K 9/48; A61K 9/64
[52] U.S. Cl. ........................ 424/456; 424/451; 424/452; 424/453; 424/460; 424/478; 424/492; 514/962
[58] Field of Search ............... 424/456, 460, 463, 478, 424/492, 451, 452, 453

[56] References Cited

U.S. PATENT DOCUMENTS

| | | | |
|---|---|---|---|
| 4,910,021 | 3/1990 | Davis et al. | 424/456 |
| 5,209,978 | 5/1993 | Kosaka et al. | 428/402.2 |

FOREIGN PATENT DOCUMENTS

| | | |
|---|---|---|
| 61-186314A | 8/1986 | Japan . |
| 380930 | 7/1989 | Japan . |
| 4159218 | 10/1990 | Japan . |

Primary Examiner—Thurman K. Page
Assistant Examiner—James M. Spear
Attorney, Agent, or Firm—Birch, Stewart, Kolasch & Birch

[57] ABSTRACT

There are disclosed herein a gelatin coating composition which comprises succinated gelatin as the main component and polyethylene glycol, and a hard gelatin capsule formed from said gelatin coating composition. The hard gelatin capsule has sufficient mechanical strength for filling operation. Moreover, it does not become insoluble due to reaction with a special drug having an aldehyde group filled therein. Therefore, it can be used for various drugs, especially macrolide antibiotics for which conventional hard gelatin capsules are inadequate.

7 Claims, No Drawings

GELATIN COATING COMPOSITION AND HARD GELATIN CAPSULE

BACKGROUND OF THE INVENTION

1. Field of the Invention

The present invention relates to a new gelatin coating composition and a hard gelatin capsule formed therefrom. More specifically, it relates to a gelatin coating composition composed of succinated gelatin (alone or in combination with unmodified gelatin) and polyethylene glycol, and a gelatin capsule made from the gelatin coating composition which easily disintegrates without becoming brittle.

2. Description of the Prior Art

Hard capsules are conventionally made from gelatin (unmodified gelatin) incorporated with a plasticizer such as glycerin and sorbitol. Such conventional hard capsules are referred to as ordinary gelatin capsules hereinafter.

Such ordinary gelatin capsules suffer from the disadvantage of having amino groups which readily react with drugs having aldehyde groups therein such as macrolide antibiotics. The reaction between the amino groups of the capsules and the aldehyde groups of the drugs gives rise to giant molecules, with the result that the capsules become insoluble to such an extent that they do not disintegrate within a certain period of time prescribed in the Pharmacopoeia of Japan. This problem is involved even in the long-term acceleration test at 40° C. and 75% RH which should be attached to the application for the drug manufacturing license.

Under the situation, the present inventors had proposed a hard capsule made from succinated gelatin. See Japanese Patent Laid-open No. 186314/1986. This capsule, however, is inferior in mechanical strength to ordinary gelatin capsules and hence it is liable to break when it is filled with drug formulation or stored for a long time. Therefore, it has not yet been put to practical use.

SUMMARY OF THE INVENTION

The present invention has been completed in view of the above situation. Therefore, it is an object of the present invention to provide a gelatin coating composition based on succinated gelatin, and a hard gelatin capsule formed therefrom which has sufficient mechanical strength required for filling operation and is inert to the drug it contains. The hard capsule is free from the problem of becoming insoluble upon reaction with the drug having an aldehyde group therein and hence it can be applied to drugs of any kind.

In order to achieve the above-mentioned object, the present inventors carried out a series of researches, which led to the finding that it is possible to improve the mechanical strength of a succinated gelatin capsule if succinated gelatin is incorporated with polyethylene glycol. Such a capsule does not react with the drug it contains and hence it can be used for a large variety of drugs. In other words, it was found that a hard gelatin capsule made from succinated gelatin incorporated with polyethylene glycol (preferably one which has a molecular weight of 1,000 to 20,000) does not become insoluble due to reaction with the aldehyde groups of macrolide antibiotics but remains soluble and readily disintegrates. Such a capsule is superior in mechanical strength to ordinary gelatin capsules. The present invention is based on this finding.

It is known that ordinary gelatin capsules are made from gelatin incorporated with polyethylene glycol. See Japanese Patent Laid-open Nos. 80930/1991 and 159218/1992. This known technology is designed to prevent ordinary gelatin capsules from becoming brittle in dry state and also from sticking to one another or to the container, and to facilitate the filling of drugs unstable to water. However, it is not intended to improve the mechanical strength of capsules. It is the present inventors' findings that polyethylene glycol imparts good disintegratability, solubility, and mechanical properties to hard capsules of succinated gelatin and hence makes hard capsules adaptable to a variety of drugs.

Therefore, the present invention provides a gelatin coating composition and a hard gelatin capsule formed therefrom, said composition comprising a gelatin material containing 50 to 100% by weight of succinated gelatin as the main component, and polyethylene glycol.

DETAILED DESCRIPTION OF THE INVENTION

According to the present invention, the gelatin coating composition is composed of a gelatin material containing succinated gelatin as the main component and polyethylene glycol, and the hard gelatin capsule is formed from this gelatin coating composition.

The succinated gelatin may be used alone or in combination with unmodified gelatin. The combined use is desirable where low cost is important. In this case, the succinated gelatin should account for more than 50% by weight, preferably more than 70% by weight, of the mixture. Otherwise, the resulting capsule would be poor in solubility when filled with some specific drugs. The succinated gelatin can be easily prepared by reacting gelatin with succinic acid anhydride.

According to the present invention, the gelatin material containing 50 to 100% by weight of succinated gelatin is incorporated with polyethylene glycol. For the resulting capsule to have improved solubility and mechanical strength, it is desirable that the polyethylene glycol has a molecular weight of 1,000 to 20,000, and it is more desirable that a mixture of two or more species be used, each having a molecular weight of 1,000, 1,500, 1,540, 4,000, 6,000 or 20,000.

The amount of polyethylene glycol to be added is not specifically limited. It should preferably be 1 to 30% by weight of the gelatin material. With an amount less than 1% by weight, polyethylene glycol would not contribute to the mechanical strength of the resulting capsule. With an amount more than 30% by weight, polyethylene glycol makes the gelatin solution cloudy and steeply lowers the viscosity of the gelatin solution, which presents difficulties in making a uniform solution and hence producing capsules of uniform thickness.

According to the present invention, the gelatin coating composition is composed of the gelatin material containing succinated gelatin and polyethylene glycol as mentioned above. They may be mixed in the usual way, which consists of allowing the gelatin material, together with water, to stand for several hours for water absorption and swelling, and adding as much polyethylene glycol in the form of aqueous solution as necessary to the gelatin material. There is obtained the desired gelatin composition in the form of jelly, which can be formed into capsules in the usual way. If necessary, the gelatin composition may be incorporated with additives, such as food dyes (designated by Pharmaceutical Affairs Laws and Food Sanitation Law) and titanium dioxide, as in the case of conventional hard gelatin capsules.

The gelatin coating composition of the present invention will find use as a raw material for capsules in the field of drugs; however, it will also find use as a raw material for containers and coating in other fields of quasi drugs, cosmetics, foods, sundry goods, etc. In the latter case, it may be incorporated with a variety of additives for individual uses.

According to the present invention, the gelatin coating composition mentioned above is formed into hard gelatin capsules. Being inert to such special drugs as have aldehyde groups, the hard gelatin capsule does not become insoluble regardless of the drug it contains. Therefore, it can be used for any kind of drugs. Moreover, it is strong enough for filling operation.

EXAMPLES

The invention will be described in more detail with reference to the following examples, which are not intended to restrict the scope of the invention.

Example 1

Succinated gelatin (7.5 kg), together with purified water (13.5 liters), was allowed to stand for about 1 to 2 hours until the former absorbed water and sufficiently swelled. The mixture was heated to 60° C. and stirred to effect uniform disolution. The resulting gelatin solution was incorporated with 1.5 kg of 50 wt % aqueous solution of polyethylene glycol having a molecular weight of 4,000. The concentration of polyethylene glycol based on the gelatin is 10 wt %. After viscosity adjustment and defoaming in the usual way, there was obtained a jelly for capsule forming. The jelly was formed into capsules (size 2) using capsule-making equipment.

Example 2

The same procedure as in Example 1 was repeated to prepare six kinds of capsules (size 2), except that the polyethylene glycol was replaced by one which has a molecular weight of 6,000 and its amount was changed to 1 wt %, 3 wt %, 5 wt %, 10 wt %, 20 wt %, and 30 wt %.

The capsules obtained in Examples 1 and 2 were evaluated by the following experiments.

Experiment 1 (Crack resistance of empty capsules)

Samples were conditioned such that their water content reached about 10%. The conditioned samples underwent the falling weight impact test (with a 49.7 g weight falling from a height of 10 cm) to examine their crack resistance. For comparison, the same test was run for ordinary hard gelatin capsules (listed in the Pharmacopoeia of Japan) and hard capsules made from succinated gelatin containing no polyethylene glycol. The results are shown in Table 1. The crack resistance was rated by counting the number of cracked samples out of 50.

TABLE 1

| Samples | Number of cracked capsules | Water content in capsules |
|---|---|---|
| Capsules produced in Example 1 | | |
| Capsules of the present invention | 6 | 8.7% |
| Hard capsules of known succinated gelatin | 48 | 10.1% |
| Ordinary hard gelatin capsules | 31 | 10.1% |

TABLE 1-continued

| Samples | Amount of PEG (wt %) | Number of cracked casules | Water content in capsules |
|---|---|---|---|
| Capsules produced in Example 2 | | | |
| Capsules of the pesent invention | 1 | 11 | 10.1% |
| | 3 | 5 | 10.0% |
| | 5 | 0 | 10.0% |
| | 10 | 0 | 9.8% |
| | 20 | 0 | 9.7% |
| | 30 | 3 | 9.5% |
| Hard capsules of known succinated gelatin | | 48 | 8.7% |
| Ordinary hard gelatin capsules | | 31 | 10.5% |

It is noted from Table 1 that hard gelatin capsules pertaining to the present invention are stronger and more resistant to cracking than ordinary hard gelatin capsules and known hard capsules of succinated gelatin.

Experiment 2 (Disintegration of capsules filled with macrolide antibiotics)

The capsules (pertaining to the present invention) produced in Example 1 were filled with 250 mg each of midecamycin, and the filled capsules were tested for disintegration according to the Pharmacopoeia of Japan XII, Item of Capsules. The disintegration test was performed on filled capsules which had been allowed to stand for 10 days at 60° C. and 75% RH. The time required for the samples to open was measured. For comparison the same disintegration test was performed on ordinary hard gelatin capsules (listed in the Pharmacopoeia of Japan). The results (in terms of an average of six measurements) are shown in Table 2.

TABLE 2

| | Samples of the present invention | Samples for comparison |
|---|---|---|
| Without conditioning | 25 sec | 1 min and 11 sec |
| With conditioning for 10 days | 24 sec | Capsules do not open. |

It is noted from Table 2 that the capsules pertaining to the present invention disintegrate more readily than hard gelatin capsules (listed in the Pharmacopoeia of Japan), and that they retain this property even after storage for a prescribed period of time.

Experiment 3 (Dissolution of empty capsules)

The capsules (pertaining to the present invention) produced in Example 1 were tested for disintegration according to the Pharmacopoeia of Japan XII, Item of Capsules. For comparison the same dissolution test was performed on ordinary hard gelatin capsules (listed in the Pharmacopoeia of Japan). The results (in terms of an average of five measurements) are shown in Table 3.

TABLE 3

| Samples | Time required for dissolution |
|---|---|
| Capsules of the invention | 1 min and 19 sec |
| Capsules for comparison | 3 min and 41 sec |

It is noted from Table 3 that the capsules pertaining to the present invention more readily dissolve than hard gelatin capsules (listed in the Pharmacopoeia of Japan).

What is claimed is:

1. A gelatin coating composition for forming a hard gelatin capsule consisting essentially of a gelatin material containing 50 to 100% by weight of succinated gelatin, and 1 to 30% by weight of one or more polyethylene glycol having a molecular weight of 1,000 to 20,000 based on the weight of the gelatin material.

2. A hard gelatin capsule formed from the gelatin coating composition defined in claim 1.

3. A gelatin coating composition according to claim 1, wherein said gelatin material contains 70 to 100% by weight of succinated gelatin.

4. A gelatin coating composition according to claim 1, wherein said polyethylene glycol comprises a mixture of two or more species having different molecular weights.

5. A gelatin coating composition according to claim 4, wherein each species of said polyethylene glycol has a molecular weight selected from the group consisting of 1,000, 1,500, 1,540, 4,000, 6,000 or 20,000.

6. A gelatin coating composition according to claim 1, wherein said gelatin composition further comprises at least a member selected from the group consisting of food dyes and titanium dioxide.

7. A gelatin coating composition according to claim 4, wherein said gelatin material contains 70 to 100% by weight of succinated gelatin.

* * * * *